(12) United States Patent
D'Antonio et al.

(10) Patent No.: US 7,086,431 B2
(45) Date of Patent: Aug. 8, 2006

(54) INJECTION CARTRIDGE FILLING APPARATUS

(75) Inventors: Nicholas F. D'Antonio, Tully, NY (US); Richard O. Colvin, Baldwinsville, NY (US); Linda F. D'Antonio, Syracuse, NY (US)

(73) Assignee: D'Antonio Consultants International, Inc., E. Syracuse, NY (US)

(*) Notice: Subject to any disclaimer, the term of this patent is extended or adjusted under 35 U.S.C. 154(b) by 85 days.

(21) Appl. No.: 10/730,147

(22) Filed: Dec. 8, 2003

(65) Prior Publication Data
US 2004/0149349 A1  Aug. 5, 2004

Related U.S. Application Data

(60) Provisional application No. 60/431,895, filed on Dec. 9, 2002.

(51) Int. Cl.
*B65B 1/04* (2006.01)

(52) U.S. Cl. .............. 141/330; 141/285; 141/286; 141/319; 141/329; 604/411; 604/414; 604/415; 222/81

(58) Field of Classification Search .......... 141/18, 141/59, 65, 67, 285, 286, 329, 330, 319; 604/411–415; 222/85, 481, 81
See application file for complete search history.

(56) References Cited

U.S. PATENT DOCUMENTS

| 4,432,755 | A | * | 2/1984 | Pearson | 141/329 |
|---|---|---|---|---|---|
| 4,697,622 | A | * | 10/1987 | Swift et al. | 141/1 |
| 5,329,976 | A | * | 7/1994 | Haber et al. | 141/25 |
| 5,358,501 | A |   | 10/1994 | Meyer et al. |  |
| 5,393,497 | A |   | 2/1995 | Haber et al. |  |
| 6,120,490 | A |   | 9/2000 | Neftel et al. |  |
| 6,503,240 | B1 |  | 1/2003 | Niedospial, Jr. et al. |  |

FOREIGN PATENT DOCUMENTS

WO    WO 01/87385    11/2001

* cited by examiner

*Primary Examiner*—Timothy L. Maust
(74) *Attorney, Agent, or Firm*—D. Peter Hochberg; Sean Mellino; Katherine R. Vieyra (57) ABSTRACT

A filling apparatus for cartridges includes a housing for holding a vial of fluid, a severing device for severing the septum of the vial, a fluid chamber for receiving the discharged fluid, a valving structure for effecting the discharge of fluid from the vial and for directing the fluid into a cartridge upon the decreasing of the size of the fluid chamber, and air inlet system for admitting air to the vial upon discharge of the fluid.

48 Claims, 7 Drawing Sheets

INJECTION CARTRIDGE FILLING APPARATUS

CROSS-REFERENCE TO RELATED APPLICATION

This application claims the benefit of U.S. provisional patent application Ser. No. 60/431,895 filed Dec. 9, 2002.

BACKGROUND OF THE INVENTION

1. Field of the Invention

The present invention deals with a handheld cartridge filling apparatus for filling the cartridge with vaccines or other fluids, and in particular to a hand-operable cartridge filling apparatus for use with needle-free ampules or cartridges and the associated filling station when dealing with multiple cartridges in a magazine.

2. Description of Prior Art

The specification of U.S. Patent Publication US 2003/0040715A1, filed Aug. 20, 2002, and corresponding PCT Publication WO 03/015846 A2, filed Aug. 21, 2002, herein incorporated by reference, describes several methods for filling ampules or cartridges prior to their use with a needle-free injection system. In particular, FIG. 19 of the foregoing earlier publications illustrate a filling station that uses a transfer syringe which first extracts the diluent from a vial supplied by the manufacturer. The syringe then transfers the diluent into a second vial containing lyophilized (powdered) vaccine. After the mixing of the diluent and the vaccine is completed, the transfer system extracts the vaccine or other medication from the vial supplied by the manufacturer. The transfer syringe containing the mixed vaccine is then placed into a described filling station and the vaccine therein is progressively transferred from the syringe into the orifice, or distal end of the empty ampules or cartridges. This filling procedure is accomplished with a simple repetitive motion of a lever which incrementally advances the syringe plunger with a positive force to move the vaccine out of the syringe and into the cartridge. Conversely, in this disclosure, suction or negative pressure is used to pull the plunger into the syringe as fluid is evacuated. Also mentioned in the preceding patent publications is the possibility of filling through the orifice end of the cartridge by pressurizing fluid in the vial to fill the cartridge without the use of a transfer syringe. It was stated in the specification of the foregoing publications, that "the main difficulty in using the vial without first transferring to the syringe, comes in the valving required to control flow of air into the vial and flow of injectate out of the vial". However, the simplified and inexpensive method of valving and pressure control as discussed in this disclosure is applied to a hand-held apparatus that houses the vial directly, and is then used to fill the ampules through the orifice end. During the development, it was realized that the handheld apparatus for transferring vaccine to the cartridges can also be used in the filling station with either the syringe or vial inserted, and is especially useful for filling multiple cartridges in a magazine format. With regard to vaccine transfer with the handheld device, neither the valving as described herein, nor the handheld device being used in the filling station option was illustrated in the earlier application.

SUMMARY OF THE INVENTION

An object of the present invention is to provide apparatus for filling one or more cartridges with vaccines or other fluids for use with injection or other devices.

Another object is to provide apparatus for discharging fluid from a standard syringe or a container having a septum over its discharge end and for filling one or more cartridges with the fluid.

A further object is to provide apparatus for severing the septum of a vial or other container to release fluid held therein into an optional metering station that will minimize lost fluid at the end of its use.

A still additional object is to provide apparatus for holding a cartridge having an openable, flexible, protective cover for maintaining sterility before, during, and after filling, and to fill the cartridge with a desired fluid.

It is a further object of the invention to provide apparatus for opening the septum of a container to discharge fluid therefrom, or alternatively, from a fluid containing syringe that has no septum, to optionally meter the discharged fluid, and to fill one or more cartridges with the fluid.

A still additional object of the present invention is to provide a hand operable, portable apparatus for discharging fluid from a container, metering the discharged fluid, and filling one or more cartridges with the fluid.

A yet further object of the invention is to provide a cartridge filling apparatus for use with cartridges having an orifice, walls defining the interior of the cartridge, and a piston disposed in the interior of the cartridge and movable from a position near the orifice end away from the orifice to define the maximum capacity of the cartridge, where the cartridge length limits the maximum amount of movement of the piston and the maximum capacity of the cartridge.

Still another object of the invention is to provide a variable size piston stop to fill the cartridge to selected amounts that are less than its maximum capacity.

It is yet still a further object of the invention to provide apparatus for opening the septum of a container holding fluid.

Still a further object is to provide an improved piercing device in apparatus for discharging fluid from a container whose discharge orifice is covered with a septum.

Another object of the present invention is to provide means for delivering air to a non-collapsible container having fluid discharged therefrom through a severed septum which had covered the discharge orifice.

Another object is to provide an optional metering station for apparatus for discharging fluid from a container.

An additional object is to provide a fluid flow system for transferring fluid from a container whose fluid contents have been discharged to an optional metering station for use in a cartridge filling apparatus.

A more specific object is to provide apparatus for removing fluid from a vial or other container holding a desired fluid and fill health care cartridges in optional metered amounts with the fluid either one at a time as in a hospital, doctor's office, research facility or at some site, or to fill a multitude of cartridges for use in a magazine for mass inoculation purposes.

Another particular object is to provide the apparatus as set forth in the preceding paragraph for use with cartridges having an orifice at one end, walls defining an interior, and a piston movable in the interior away from the orifice as fluid is transferred to the cartridge, the final position of the piston determining its capacity.

Another specific object of the invention is to provide a hand operable apparatus for filling cartridges as set forth in the preceding paragraph which is compact, easy and efficient in use, inexpensive and efficient and long lasting in operation.

These and other objects will be apparent from the description to follow and from the appended claims.

The invention includes in one respect apparatus for opening the septum of a vial or other container upon the insertion of the container into the apparatus. The apparatus in this respect is a housing having a septum severing device in the form of a spike for piercing the septum when the container is inserted into the apparatus. The spike includes a conduit for discharging fluid from the container and has a one-way valve for controlling the flow from the container. The spike further has another conduit through which atmospheric air can enter the container, also having a one-way valve. Alternatively, a fluid containing syringe can be inserted into the apparatus so that its exit nozzle interfaces with the fluid flow conduit, in which case, there is no septum or septum severing device, nor is there a conduit for the inflow of atmospheric air since the syringe plunger is always pulled into direct contact with the fluid surfaces as the fluid is extracted during the filling process.

The invention includes in another respect a discharge device including an optional metering structure having a chamber with a cavity of variable size to receive desired amounts of fluid for transfer to the cartridge. A tubular member (which is preferably cylindrical but could be of any shape) conveys the fluid from the metering structure to the cartridge. A tubular member has a one-way valve for preventing the leakage of fluid when there is no cartridge positioned to receive the fluid.

According to one preferred embodiment of the invention, the discharge device is in the form of a cartridge interface device or cartridge receiver which has both a cartridge positioning device for positioning a cartridge to receive the fluid, and walls for cooperating with the housing to define an optional metering station. A spring structure biases the housing to cause the cavity of the metering station to assume its largest size. A tubular rod from the metering station defines a path for fluid to flow from the metering station to the cartridge.

In another preferred embodiment of the invention, the discharge device includes spring biased walls which cooperate with walls from the housing to define an optional metering structure. A cartridge positioning device locates a cartridge between the walls, and the amount the cartridge extends between the walls when force is applied to the housing to move the housing and metering structure over the cartridge, determines the size of the metering station. In both of the preferred embodiments, the spring structure returns the unit to its initial position after the cartridge has been filled.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF THE PREFERRED EMBODIMENT

The invention involves a system for filling cartridges with fluid from a container by creating an air pressure differential across fluid in the container, where the container can be a non-collapsible container having a septum for closing a discharge orifice or a collapsible container such as a syringe with a piston which can be used to discharge fluid from the syringe. The inventive system includes a holder for holding the container, and an air pressure differential apparatus having walls defining a variable size chamber which is connected to the container. The walls are movable to expand or decrease the size of the chamber. When the chamber is in one of its expanded or decreased sizes (depending on the embodiment), fluid is drawn from the container—and when the chamber is moved to its other sizes, fluid is transferred into a cartridge. In one embodiment, a variable size chamber both forces air into the container and receives fluid from the container, from whence it is transferred to a cartridge. In another embodiment, the variable size chamber holds air in its expanded size, and establishes a pressure differential across the fluid in the container to force fluid from the container. A second or fluid chamber receives fluid from the container for transfer to a cartridge.

Referring now to the drawings wherein the showings are for the purpose of illustrating the preferred embodiment of the invention only, and not for the purpose of limiting same, the attached figures illustrate two embodiments of a hand-held ampule or cartridge filling apparatus discussed above, or alternatively, for insertion into a filling station as described below for FIG. 4A, FIG. 4B and FIG. 4C. FIG. 2B and FIG. 3 are enlarged and do not necessarily resemble actual dimensions. (The term "fill" refers to the amount of fluid transferred to a cartridge, which can be any amount up to the maximum capacity.) For example, spike 23 and 23' (described below) are less than one-eighths (⅛) inch in diameter and take very little space when inserted into the septum end of a non-collapsible vial 12 (also described below). Likewise, channels 28 and 30 (described later) inside septum spike 23 are less than 1 mm. in diameter. However, the figures are used to clearly illustrate and describe the embodiments of the invention.

Figure 1:
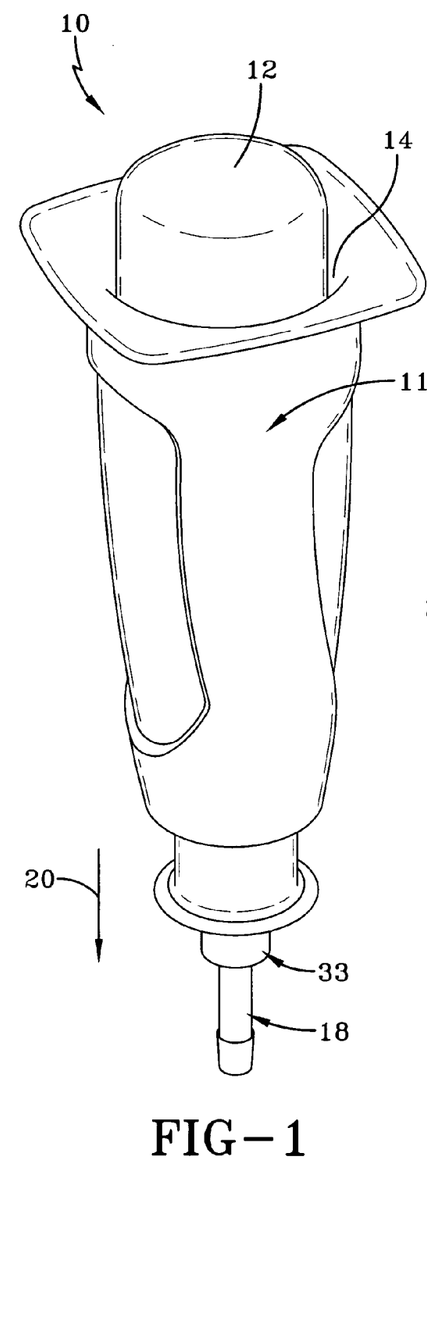
FIG. 1 is a front perspective view of a filling apparatus.
Figure 2A:
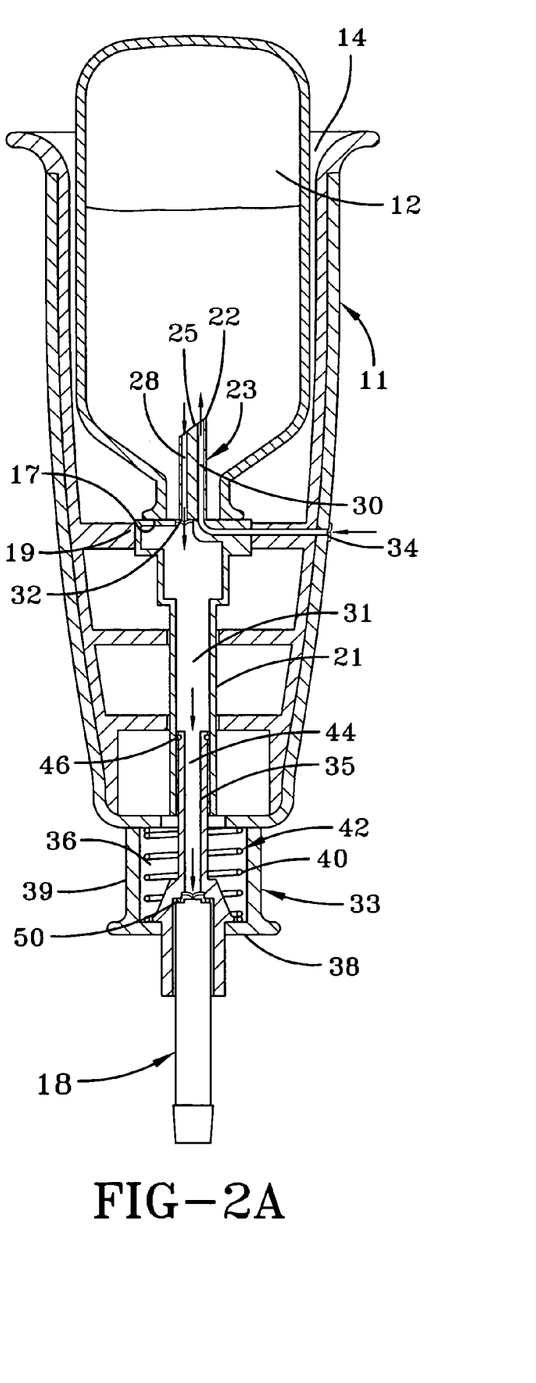
FIG. 2A is a perspective cross section of the filling apparatus of FIG. 1 showing positioning of the vial when inserted for transfer of the fluid.
Figure 2B:
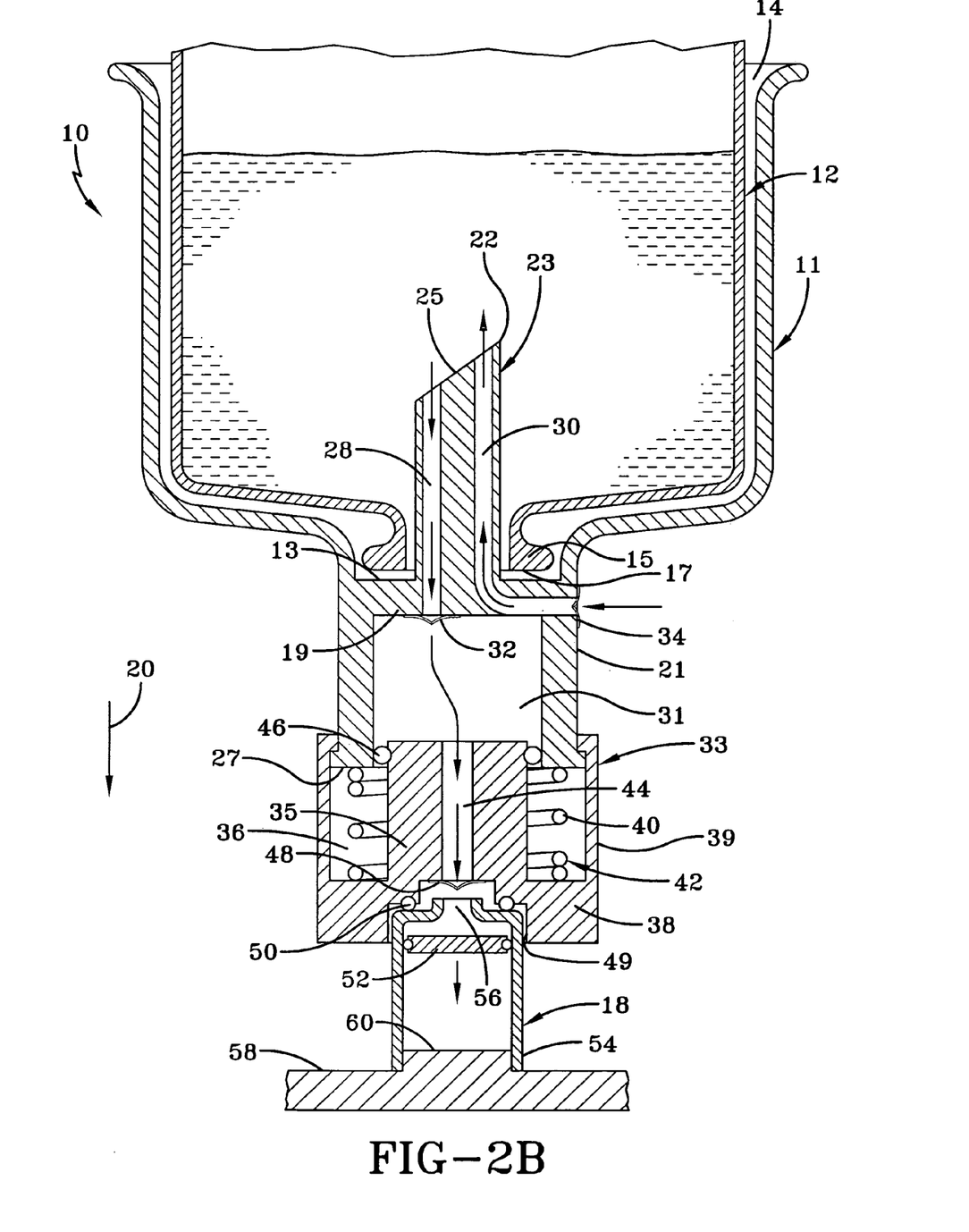
FIG. 2B is an enlarged schematic cross section of a simplified series of elements for the inner structure of FIG. 2A showing the, spring, valves, and flow path for the fluid into the cartridge and the venting path for air into the vial.
Figure 3:
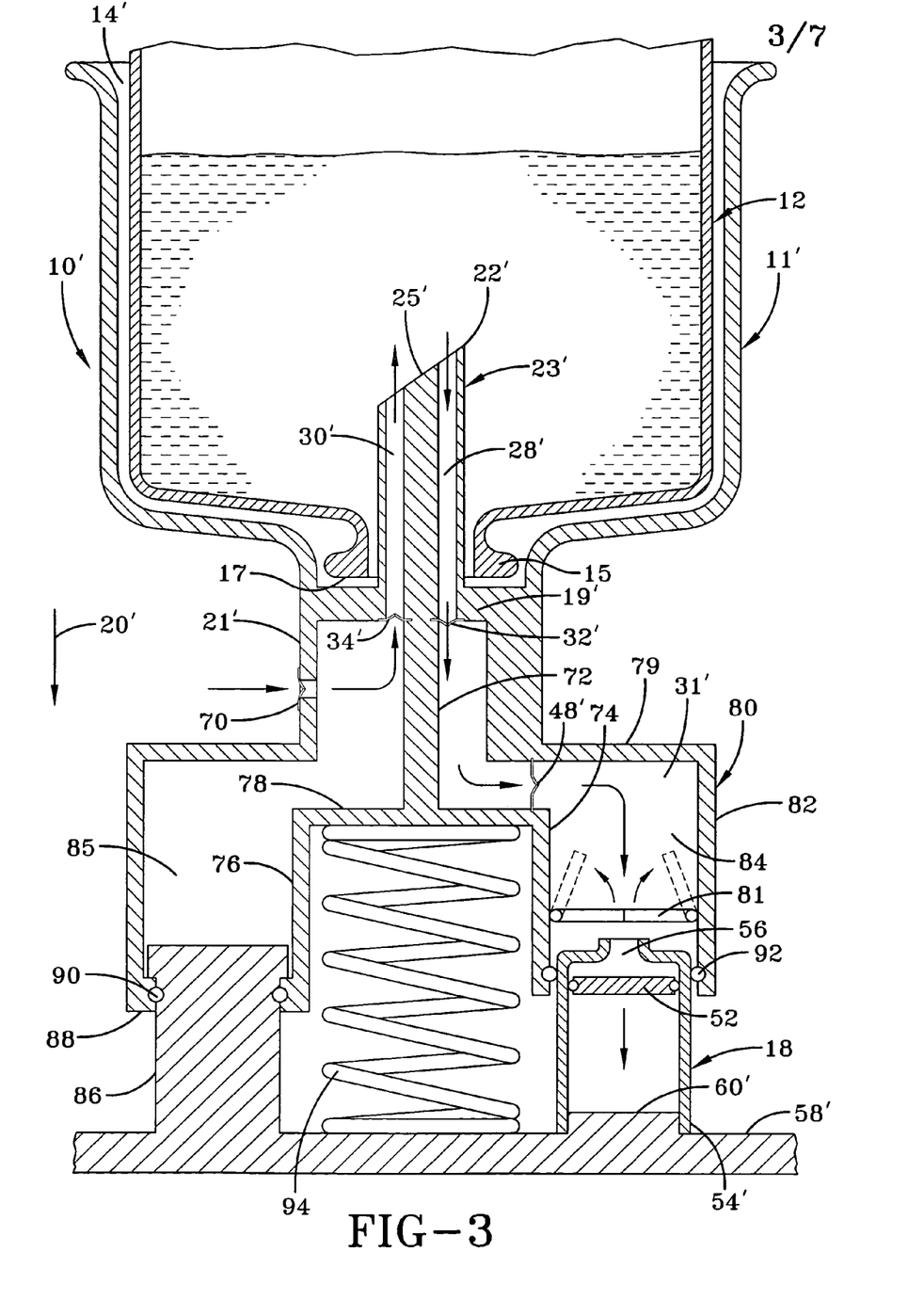
FIG. 3 is also an enlarged schematic of a simplified cross section of another embodiment of the filling apparatus showing a reversal of the forces related to the air and fluid flow from that of FIG. 2B.

FIGS. 1, 2A, 2B and 3 disclose a cartridge filling apparatus 10, which houses a vial, bottle or similar vessel or container 12 for holding vaccine or the like when it is inserted into an opening 14 in a flared open housing or handpiece or holder 11. The assembly shown in FIG. 2A is very similar to that shown in FIG. 2B, but there are some differences regarding some of the details. FIG. 2A is similar to a prototype injection cartridge filling apparatus whereas that of FIG. 2B has been modified for ease of explanation. Housing 11 (the apparatus connected to housing 11 as described below are referred to as container holder wall structure) is a hollow, preferably truncated rounded cone-like structure. Housing 11 includes a shoulder 13 for receiving a rim 15 of the septum end 17 of vial 12, which rim 15 abuts against the shoulder 13. Housing 11 has an interior diameter dimensioned to receive the body of the largest vial 12 anticipated, but smaller vials can also be used. A bored collar 19 extends across a relatively large bored neck 21 (different versions are shown in schematic FIG. 2B and the prototype of FIG. 2A) of housing 11. A wall 25 extends through a severing device, such as a bored spike 23 with a piercing point 22, and forms with spike 23 two channels or conduits 28 for fluid flow and 30 for airflow, whose paths are fully isolated from each other. A vaccine or other fluid compartment 31 is formed between collar 19 and the upper free end of inner tubular cylindrical wall or rod 35 as discussed below. Housing 11, as shown in FIGS. 1 and 2A, extends over most of the wall except for a cartridge interface device, cartridge receiver or nosepiece 33 as discussed below.

At the insertion of vial 12, the septum on end 17 of vial 12 is punctured by piercing spike 23. Channel 28 includes a one-way valve 32 for discharging vaccine (or other fluid) out of vial 12 and into an optional metering station such as a metered compartment, internal vaccine chamber or variable chamber 31. While being metered not necessary for effective operation, chamber 31 can be designed to hold the maximum amount of fluid to be transferred and limits the amount of fluid discharged each time it is used. The second channel or conduit 30 has a one-way valve 34 for admitting atmospheric air into vial 12 as the vaccine (or other fluid) is extracted. While both one-way valves 32 and 34 are shown as conventional and inexpensive duckbill valves, other one-way valve types such as an umbrella valve, a flap valve or a ball and socket valve will work as well. Metering compartment 31 is thus a collapsible, variable size chamber having a relative large cavity when in its open or expanded state, and a relatively small cavity when in its closed or decreased size state (as discussed herein).

Apparatus 10 is used for filling cartridges or ampules 18 as discussed below. Apparatus 10 further includes cartridge interface device, a cartridge receiver or nosepiece 33. Interface device 33 has an outer cylindrical wall 39 and inner tubular cylindrical wall or rod 35 to define between them a cylindrical chamber or receptacle 36 closed at its distal end by a generally cylindrical ring 38. Neck 21 of housing 11 is extendible into chamber 36, and one or more springs or other biasing device 40 supports housing 11 and vial 12 (if disposed in housing 11) to form a spring valve subassembly 42. (Biasing device 40 as shown in FIG. 2A is covered by nosepiece 33, shown as an extension of housing 11.) Rod 35 has a longitudinal bore or conduit 44. A seal 46 prevents the flow of liquid between neck 21 and rod 35 as discussed below. A low pressure cracking valve 48, also discussed below, extends across bore 44 of rod 35. The term "discharge device" refers to the part of the interface to form the optional metering station and the member defining the fluid flow path to the cartridge.

Cartridge receiver 33 further includes a receptacle or receiver end 49 for interfacing with the filling end of a received cartridge 18. A seal 50 prevents the leakage of liquid from the space between received cartridge 18 and the wall-defining receptacle 49.

Cartridges 18 each have a generally cylindrical inside chamber. A longitudinally movable cartridge piston 52 is disposed in the chamber. Cartridges 18 each have a cylindrical base 54 and open entrance end or orifice 56.

A platform 58 is provided for receiving base 54 of each of cartridges 18 and has a protrusion or appendage 60 for extending into the space in base 54 of cartridge 18. Piston 52 forms the movable bottom of cartridge 18. As explained later for FIG. 5, cartridge 18 usually has an openable, flexible sheet across its orifice. As interface device 33 is moved down over the end of cartridge 18, it opens the sheet to provide and maintain a completely sterile access to the orifice, before, during, and after the filling process.

In its operation, cartridge receiver 33 of apparatus 10 is placed over the orifice 56 interface of cartridges 18. (As discussed below, cartridges are held in a magazine.) The entire housing 11 is then forced downward as shown by direction arrow 20. This action forces rod 35 upward relative to housing 11 against spring valve subassembly 42. As rod 35 is forced upward into internal vaccine compartment 31, compartment 31 decreases in size, and the vaccine (or other fluid) contained therein is forced downward through bore 44 in rod 35 and into orifice 56 of cartridge 18 to discharge the vaccine (or fluid) into cartridge 18. This motion forces the cartridge piston 52 to the proximal end of cartridge 18 as described above. Low cracking pressure valve 48 prevents leakage when no cartridge at all is located in a receiver end 49 which positions or registers the cartridge to receive the vaccine (or fluid). Appendage 60 on support platform 58 stops piston 52 when cartridges 18 are filled to the selected amount. Appendage 60 can be supplied in a variety of sizes to vary the dose cartridges 18 are capable of taking.

When the force movable in direction of force vector 20 is removed from housing 11, biasing device 40 will return rod 35 to its extended position. This action provides a vacuum force in chamber 31 and a new supply of fluid is drawn into chamber 31 through one-way valve 32 from vial 12. The removal of fluid from non-collapsible vial 12 causes a slight vacuum therein; therefore, atmospheric one-way valve 34 in the air vent path 30 of spike 23 admits enough atmospheric air to relieve the vacuum. This action/reaction assures easy withdrawal of vaccine for the next cycle.

FIG. 3 is a second embodiment of the handheld concept disclosed herein, again enlarged, and with similar functions having the same numbers as those in FIG. 2A and FIG. 2B, but with prime superscripts in FIG. 3. While the force vectors for the transfer of fluid and airflow are reversed from that of FIGS. 2A and 2B (i.e., negative pressure fills fluid chamber 31 in FIG. 2B and positive pressure fills fluid chamber 31' in FIG. 3), this embodiment is also capable of being used with a filling station apparatus similar to that shown and described below with respect to FIGS. 4A, B and C.

A cartridge filling apparatus 10' of FIG. 3 includes a handpiece or housing or holder 11' having walls for receiving vial 12. Housing 11' is as before a generally truncated, flared core-like structure with an opening 14'. Housing 11' has a bored collar 19' against which rim 15 of septum 17 of vial 12 can abut. Bored collar 19' (as stated previously, collar 19' and other components connected to housing or vial 11' are referred to as "container holder wall structure") has extending therefrom bored bottle spike 23' with piercing point 22'. Wall 25' cooperates with spike 23' to define channels 28' (for fluid flow) and 30' (for airflow). One-way valve 34' is located in channel 30' for admitting air into vial 12 and one-way valve 32' is disposed in channel 28' for discharging vaccine (or other fluid) from vial 12. A one-way air valve 70 extends through neck 21'. A wall or post 72 depends from wall or center post 25' of septum spike 23 to fully isolate an air side or variable size chamber 85 from the fluid side of bored collar 19', and has at its end a cylindrical structure 74 with a cylindrical wall 76 and a cap 78.

Housing 11' has an enlarged, open cylindrical portion 80 having within it a cylindrical wall 82 which cooperates with wall 74 also within portion 80 and on the interior thereof to define a portion of a cylindrical compartment or fluid chamber 84. Low pressure cracking valve 48' extends between cap 78 and a horizontal wall 79 of portion 80 for admitting fluid from vial 12 into metered fluid compartment 84 and then into the orifice 56 of cartridge 18. The bottom portion of cylindrical compartment 84, just above the point where it interfaces with cartridge 18, has a door structure 81 that will open as cartridge 18 advances into compartment 84 while filling, and closes when cartridge 18 is pulled out, and will prevent the leakage of fluid (vaccine) in the absence of cartridge 18. Door structure 81 defines a second portion of fluid chamber 84. In this embodiment, the discharge device refers to cartridge 18 and the member defining the fluid flow path to the cartridge.

A cylindrical structure 86 extends from platform 58' for reception into open end 88 of air compartment 85. An air seal 90 is between the outer wall of cylinder 86 and the walls defining compartment 85. A fluid seal 92 is located between walls 76 and 82 for engaging cartridge 18 when it extends into compartment 84. Cartridge 18 has piston 52 as discussed earlier. Platform 58' has protrusion 60' for entering the base opening of cartridges 18. A compressible spring assembly 94 extends between cylindrical structure 74 and platform 58'.

In operating the FIG. 3 embodiment, force vector 20' pushes vial 12 and housing 11' (and container holder wall structure) downward against stationary platform or device 58' containing cylindrical member 86 and cylindrical cartridges 18. Entrance of cylindrical member 86 into air-containing compartment 85 forces air into vial 12 through one-way valve 34'. The resulting pressure in vial 12 forces vaccine through exit one-way valve 32' and into the orifice, or distal end 56, of cartridge 18. Pushing vial 12 in the downward direction also compresses spring 94, and therefore removal of force vector 20' from vial 12 allows spring 94 to push cylindrical structure 74 and housing 11' away from cylindrical member 86 whose function is that of a pump. Removal of cylinder 86 creates a vacuum in compartment 85 and therefore permits the entrance of atmospheric air into compartment 85 through one-way valve 70 in preparation for the next cycle. Conversely, filling apparatus 10' of FIG. 3 can also be used with vial 12 and housing 11' held stationary, and cylinder 86 and cartridges 18 are pushed toward vial 12 and housing 11' to provoke the filling process. As explained earlier, seal 90 prevents the leakage of air when housing 11' and compartment 85 move over cylinder 86, and seal 92 prevents leakage of fluid when the housing moves over cartridges 18. As explained later for FIG. 5, but not shown in FIG. 3, the openable, flexible cover on cartridge 18 is opened as the lower portions of walls 82 and 74 approach the orifice end of cartridge 18.

Figure 4A:
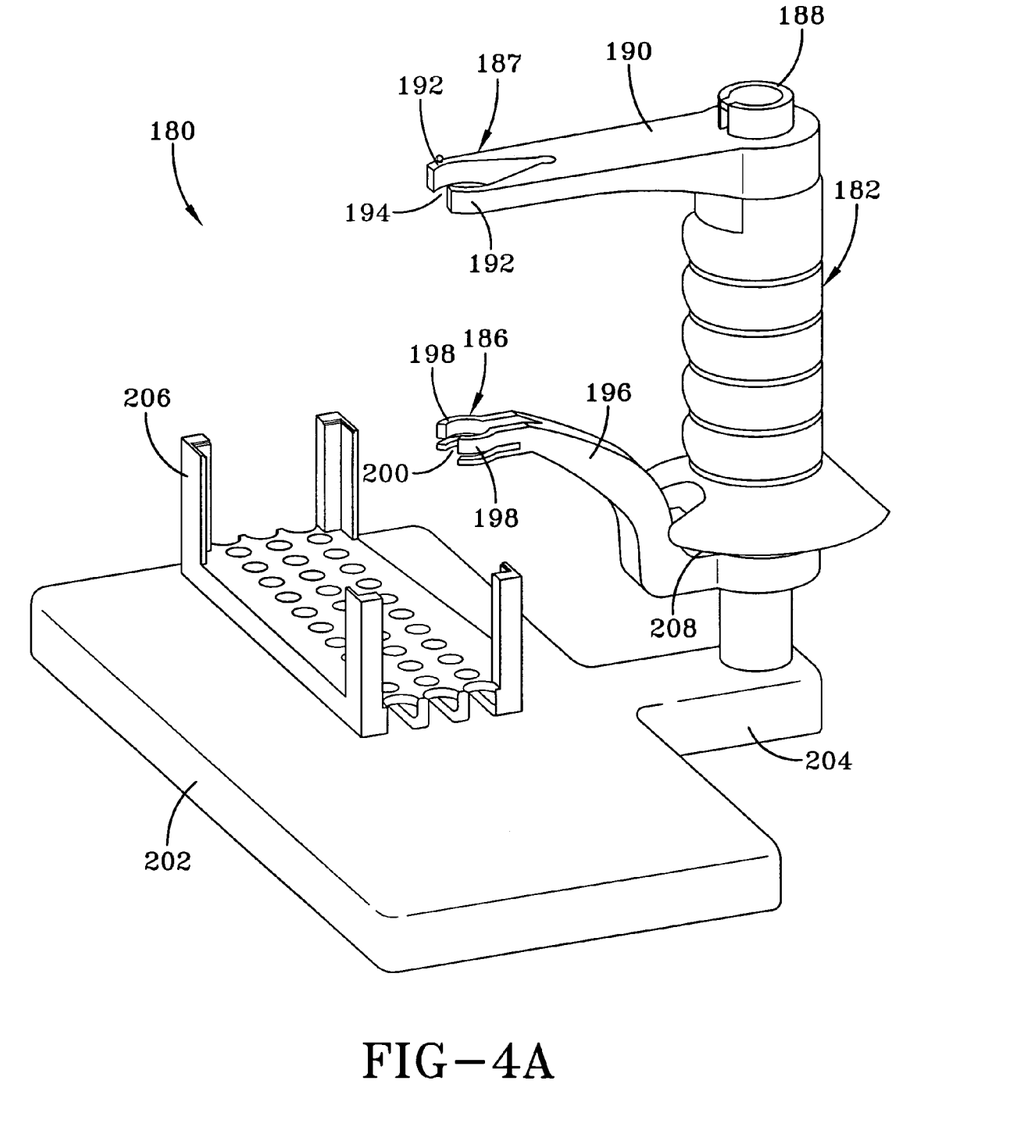
FIG. 4A is a perspective view of a filling station prior to insertion of the filling apparatus shown in FIG. 1, FIG. 2A and FIG. 2B.

FIG. 4A shows a filling station 180 before the handheld filling apparatus of FIG. 1, FIG. 2A, or FIG. 2B has been inserted for the filling of cartridges contained in a magazine structure described for FIG. 5 below. However, filling station 180 could be configured for the embodiment of FIG. 3 as well. Filling station 180 includes a handle assembly 182 having an upper jaw 187, a lower jaw 186 and a jaw-connecting column 188. Upper jaw 187 has a vertically-movable flange 190 with forked support arms 192 defining a gripping portion 194 for holding an intermediate portion of an inverted manual cartridge-filling apparatus such as apparatus 10. Lower jaw 186 includes an upwardly curved and vertically movable flange 196 having forked gripping arms 198 defining a gripping portion 200 for gripping the lower portion of an inverted cartridge-filling apparatus 10. When handle 182 is grasped and moved downwardly, upper flange 190 and lower flange 196 initially move together against the bias of a compression internal spring mechanism 199, and in doing so, advances the entire housing 11 (when inserted) toward the cartridge orifice for filling. After contact with the orifice is made, lower flange 196 becomes stationary, and upper flange 190 continues to move housing 11 forward or downward when inserted, against the pump spring in apparatus 10. This downward motion will close gap 208 to execute the filling of cartridge 18 as described earlier for FIG. 2B.

Filling station 180 further includes a platform 202 having an extension 204 for supporting handle assembly 182 with flanges 190 and 196. Located on platform 202 is a sliding magazine holder 206 that will progressively advance the cartridges held in magazine 206 to the interface with the filling nozzle of structure 11, when inserted in filling station 180. In its operation, filling station 180 of FIG. 4 will accept filling apparatus 10 in jaw structure 186, 187. Handle 182 of filling station 180 is forced downwardly against internal spring mechanism 199. When cartridge filling is completed, internal spring mechanism 199 will return handle 182 to its initial position in preparation for the next fill cycle. This downward motion provides force vectors 20 as described above for the handheld operation of filling apparatus 10 described with respect to FIG. 1, FIG. 2A, FIG. 2B and FIG. 4.

Figure 4B:
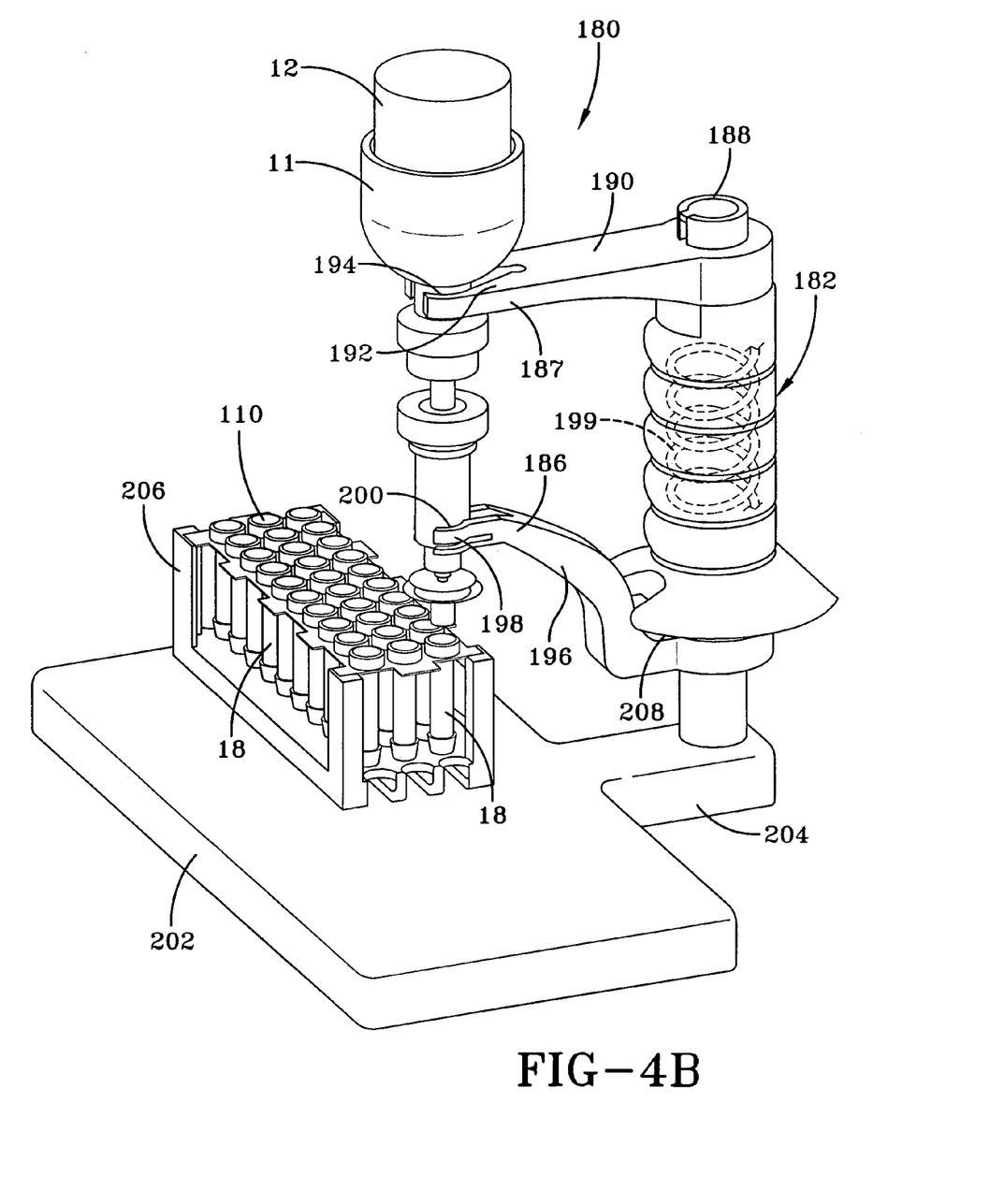
FIG. 4B is a perspective view of the FIG. 4A filling station with the medication vial of FIG. 1, FIG. 2A and FIG. 2B inserted in the filling apparatus.
Figure 4C:
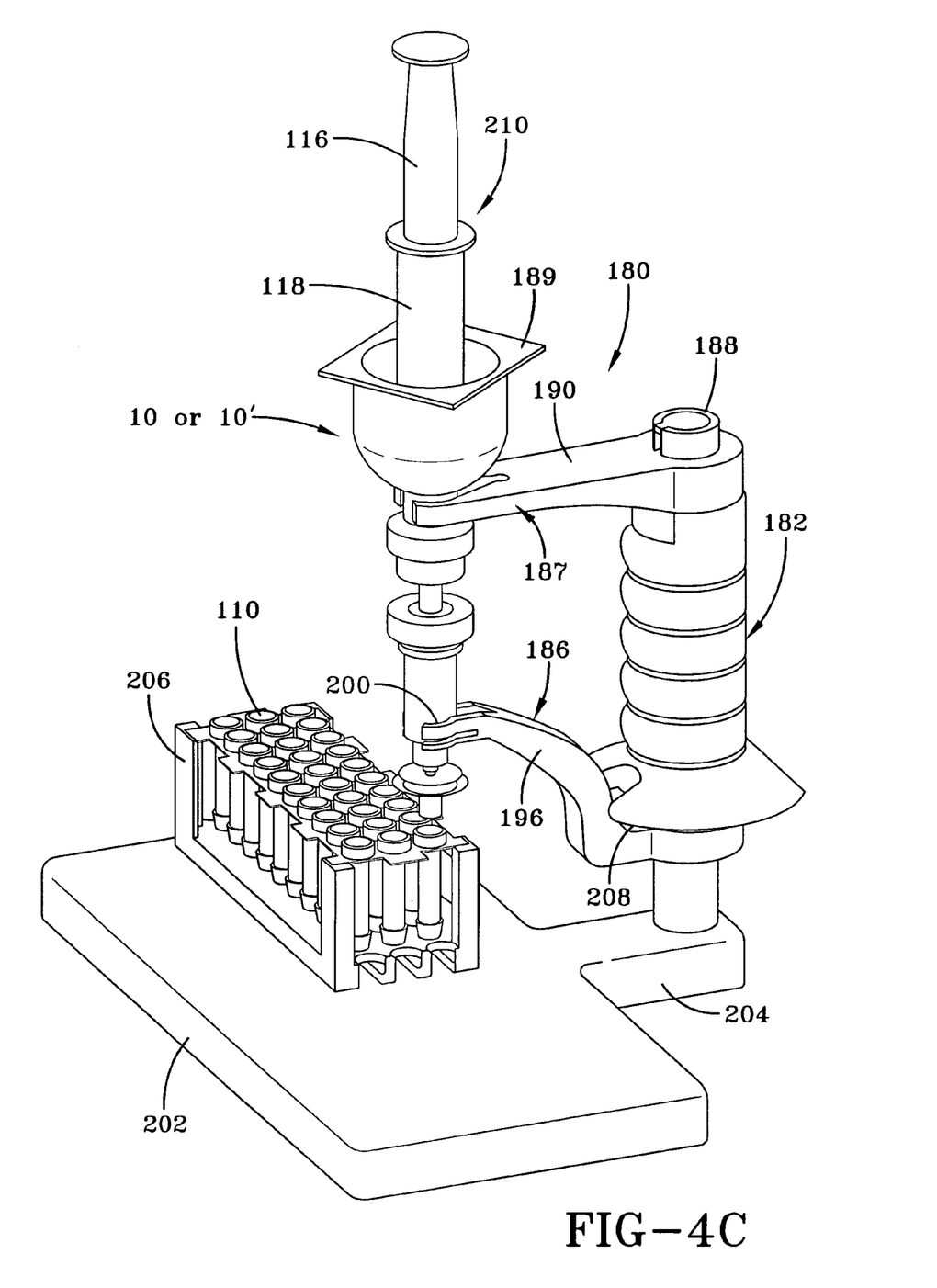
FIG. 4C is a perspective view of a filling station with the transfer syringe inserted in the filling apparatus.

FIG. 4B shows filling station 180 now housing the manufacturer's vial for the direct filling of cartridges from the vial with the use of apparatus 10 as described above with respect to FIG. 1, FIG. 2A and FIG. 2B. FIG. 4C, on the other hand, shows the same filling station housing the transfer syringe 210 (as described earlier) comprising syringe body 118 and moveable syringe plunger 116 for filling the cartridge, and this structure is similar in appearance to that described in U.S. Publication 2003/0040715A1, which requires the application of a positive force on the syringe plunger to facilitate filling of cartridge 18. In the case of FIG. 4C, and as described in the earlier case, the syringe is still used for first mixing the vaccine, after which it pulls the mixed fluid from the manufacturer's vial before insertion into apparatus 10. Accordingly, apparatus 10, with syringe 210 in place, is connected to filling station 180, but in this case, the negative pressure described for the vial-direct apparatus of FIG. 4B now serves to pull a plunger or plunger rod 116 downward as fluid is extracted from syringe body 118. To facilitate cartridge filling with the syringe embodiment, and as described in FIG. 4B, flanges 190 and 196 are moved downward at the same time when handle 182 is moved in the downward direction. When contact is made with the cartridge, flange 196 becomes stationary, but flange 190 continues to move downward to facilitate filling the cartridge as gap 208 is closed. Alternatively, rather than using handle 182 for providing the downward motion, FIG. 4C allows for filling the cartridge by pressing on a set of wings 189 (downward force on piston 116 is not necessary as described for FIG. 19 from the earlier case) to provide the filling procedure described above. When handle 182 (or wings 189) is released, spring force returns handle 182 (and wings 189) to its uppermost position which creates a vacuum in chamber 31. The vacuum in chamber 31 will pull plunger 116 into direct contact with the surface of the fluid as it is evacuated from syringe body 118. Since plunger 116 is always in direct contact with the surface of the fluid, there is no need for an air vent, a septum, or a septum spike as described for the non-collapsible vial described for FIG. 2A. Consequently, for the syringe shown in the FIG. 4C embodiment, septum spike 23 is removed (twist turn or press fit) and inserted in its place is the exit nozzle of syringe 210 whose flow path will provide fluid flow channel 28 as described for FIG. 2B. Laminated covers through which the sterile filling process is performed (FIG. 5 below) is shown covering the cartridge orifice for both the FIGS. 4B and 4C embodiments.

Figure 5:
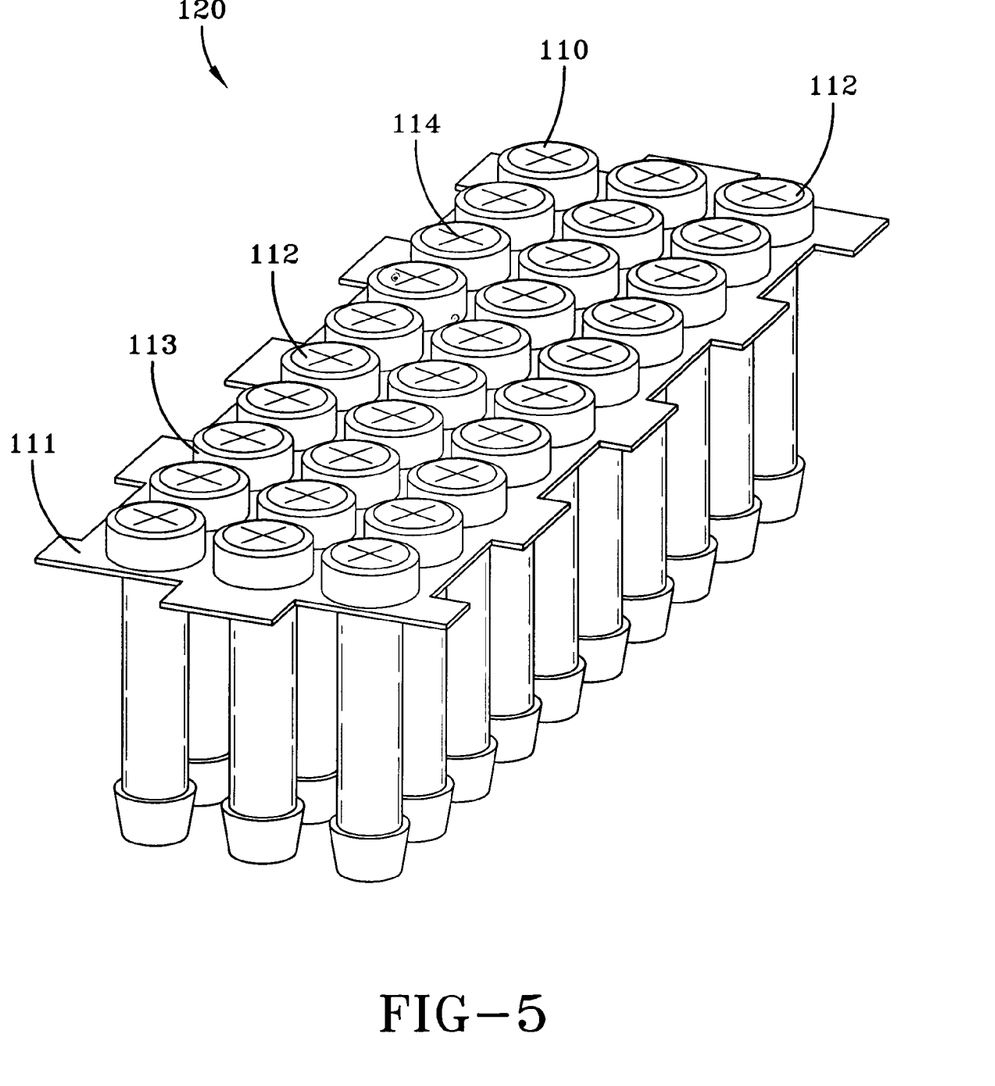
FIG. 5 is a disposable, sterile magazine, illustrating the structure for holding 30 cartridges ready for the sterile filling procedure as shown in either of FIG. 4B or 4C.

The filling station described in U.S. Patent Publication US 2003/0040715A1 includes a disposable magazine similar in nature to that shown herein in FIG. 5. This magazine concept 120 has the features listed below and includes a laminated cover 110 to protect the orifice end of the cartridges 18 therein providing for complete sterility before, during, and after filling. The disposable magazine 120 can be made of low-cost plastic and can have the orifice end of the cartridges installed via friction fit in mating depressions 112. Laminated cover 110 can be made of foil and Mylar to protect the orifice, as well as for providing for efficient sterilization, packaging and shipping of the magazine and its cartridges. Cover 110 can be applied over the filling access ports, i.e., orifices 56, but need not be removed to fill the cartridges. Cover 110 thus includes a flat section 111 and integral protrusions 113 for receiving the upper parts, or orifice end, of cartridge 18. When considered for use with the embodiment of FIG. 2B, the lamination is designed to yield with the application of pressure from the forwardmost end of cylindrical chamber 36 comprised of distal end cylindrical ring 38 when it advances to make access to the orifice during filling. At this time, the lamination of cover 110 will be forced to the open position with the first advance of the outer ring 38 on receiver end 49 of apparatus 10 or the lower portions of walls 76 and 82 of apparatus 10' when used with the embodiment of FIG. 3. As the opening occurs, neck 21 or 21', that transfers the vaccine, will advance through cylindrical chamber 36 (FIG. 2B) or lower portions of walls 76 and 82 (FIG. 3), makes contact with cartridges 18, and filling takes place through orifice 56. Since neither the filling nozzle nor orifice 56 makes any contact with outside surfaces, the procedure is free from the risk of contamination. The lamination consists of a foil top layer that provides a protective seal for the space in front of the orifice. Depression in the foil after filling provides a visual indication that a cartridge has been filled. The second layer 112 of the lamination is made from a material such as Mylar that can spring back to its original position and reseal the surface after penetration from the filling nozzle is removed. Layer 112 is pierced with contact and force on the frangible "X" pattern 114, coincident with each of the filling access openings in the disposable magazine. When the filling interface is pressed through the foil layer, "X" pattern 114 opens downward and outward from the center to allow the filling interface to seal against the cartridge nozzle. When the filling interface is withdrawn, the "X" pattern provides a visual change at the frange lines when it returns to its original position, thus protecting the orifice from external contamination as described above. There could be a third, resealable top layer (not shown) that can be pulled away to expose the foil and replaced after filling to further enhance protection.

The invention has been described with particular emphasis on the preferred embodiment. It should be appreciated that these embodiments are described for purposes of illustration only, and that numerous alterations and modifications may be practiced by those skilled in the art without departing from the spirit and scope of the invention, it is intended that all such modifications and alterations be included insofar as they come within the scope of the invention or the equivalents thereof.

The invention claimed is:

1. Apparatus for filling at least one fluid cartridge with a fluid, the at least one fluid cartridges having opposing ends, a fluid cartridge orifice in one of said ends, and a piston inside the fluid cartridge for defining a fluid container between the piston and the fluid cartridge orifice, the piston moving away from the orifice as fluid enters the container, said apparatus comprising:

a housing for receiving a container holding the fluid, the container having a fluid discharge orifice covered by a septum;

a septum opening device affixed to said housing and independent of the fluid cartridge(s) for severing the septum in response to the relative movement of the container with respect to said septum opening device; and a protrusion for receiving the outer surface of the fluid cartridge piston for determining the maximum amount of fluid for reception by the fluid cartridge.

2. Apparatus for filling at lest one fluid cartridge with a fluid, the at least one fluid cartridges having a wall and an entrance orifice, said apparatus comprising:

a housing for receiving a container holding the fluid, the container having a fluid discharge orifice covered by a septum, the housing including a container support for supporting a container in an inverted position with the septum covered discharge orifice facing downward;

a septum opening device affixed to said housing and independent of the fluid cartridge(s) for severing the septum in response to the relative movement of the container with respect to said septum opening device;

a metering station for receiving an amount of fluid from the container for transfer to a fluid cartridge, said metering station comprising:

a chamber defined by first walls fixed with respect to said housing, and second walls, said first and second walls having an open position for defining said chamber to form a relatively large cavity and a closed position for defining said chamber to form a relatively small cavity, and being movable with respect to each other to compress said chamber and force fluid from said chamber into a fluid cartridge, a spring structure for biasing said first and second walls to the open position;

a fluid cartridge receiver comprising:

said second walls for cooperating with said first walls to define said chamber; and channel walls defining a channel for providing a fluid path delivering fluid from said metering station to a fluid cartridge; and a one-way valve in said channel for preventing the flow of fluid from said metering station where there is no fluid cartridge to receive the fluid.

3. Apparatus according to claim 2 and further comprising:

a valve for opening for transmitting a predetermined amount of fluid from a container to a fluid cartridge, and for closing when transmission of the predetermined amount of fluid is completed.

4. Apparatus according to claim 2 and further comprising a conduit for defining a path for fluid from the container to said metering station, and a conduit defining a path for atmospheric air to the container, said conduits defining the respective paths in response to the severing of the septum on the container.

5. Apparatus according to claim 4 and further including a fluid conduit for entering a container supported in said housing, said fluid conduit including a one-way valve for releasing fluid from the container to said metering station.

6. Apparatus according to claim 4 and further including an air conduit for transferring air to the container, and a one-way valve for admitting air to the container.

7. Apparatus according to claim 2 wherein the fluid cartridge is covered with an openable cover, and wherein said second walls include a cover opening portion for opening the openable cover over the orifice of a fluid cartridge for defining a sterile procedure for fluid access to the fluid cartridge before, during and after filling.

8. Apparatus for filling at least one fluid cartridge with fluid, the fluid cartridge having an orifice at one end, said apparatus comprising:
   a housing for receiving a container holding the fluid, the container having a rim defining a discharge orifice and a septum over the orifice, said housing comprising;
      a container holding portion for holding a container in an inverted position with the septum covered orifice facing downwardly;
      a container support for supporting the container rim and the container, said container support having a bored spike independent of the fluid cartridge(s) for piercing the septum, said bored spike having both a fluid conduit for discharging fluid from the container with a one-way valve for preventing leakage through the fluid conduit and an air conduit for the flow of atmospheric air into the container with a one-way valve for preventing the flow of fluid or air through said air conduit out of the container; and
      a neck portion forming part of a collapsible chamber of a metering station; and
   a fluid cartridge receiver fixed relative to said housing, said fluid cartridge receiver comprising:
      metering structure for cooperating with said neck portion of said housing to form the collapsible chamber of said metering station; and
      a tubular member extending from said metering station for defining a fluid flow path from said metering station to a fluid cartridge, with a one-way valve in said tubular member to prevent leakage of fluid from said tubular member when no fluid cartridge is present in said receiver.

9. Apparatus according to claim 8 and further comprising:
   a biasing device for biasing said housing away from a fluid cartridge to enlarge the size of the chamber of said metering station.

10. Apparatus according to claim 9 and further comprising:
   a platform for supporting at least one fluid cartridge to be filled, said platform having at least one protrusion for extending into the end of a fluid cartridge opposite the orifice end of the fluid cartridge for establishing the maximum content of the fluid cartridge.

11. Apparatus according to claim 10 and further comprising:
   an interface device for interfacing a fluid cartridge with said apparatus, wherein said tubular member extends between said metering station and said interface device for defining the fluid flow path from said metering station to the fluid cartridge.

12. Apparatus according to claim 11 wherein the orifice of the at least one fluid cartridge is covered with an openable flexible sheet, said apparatus further comprising:
   an orifice sheet opener for opening the sheet covering the orifice of the fluid cartridge to provide access to the orifice of the fluid cartridge;
   wherein when a fluid cartridge is disposed in said interface device and force is applied to said housing to cause the orifice sheet opener to open the sheet covering the orifice of the fluid cartridge and to decrease the size of said metering station, to force fluid from said metering station, through said tubular member, through the opened sheet cover of the fluid cartridge and into the fluid cartridge, fluid being discharged from the container through said container conduit and air being admitted to the container through said air conduit, said housing being thereafter moved to enlarge the size of the chamber of said metering station upon the filling of the fluid cartridge with the fluid.

13. Apparatus for filling fluid discharged from a container, at least one fluid cartridge, the fluid cartridge having an orifice at one end and an opposing end, and a piston inside the cartridge for defining a fluid-containing portion between the piston and the orifice, and for holding the fluid cartridge to receive the discharged fluid, said apparatus cooperating with structures forming one portion of a metering station having a variable size chamber for holding fluid from the container prior to the transfer of the fluid to the fluid cartridge, said apparatus comprising:
   an interface device comprising:
      a second portion of the station for cooperating with the one portion of the metering station;
      a receiver end for receiving the fluid cartridge to be filled with fluid;
      a tubular member extending between the metering station and said receiver end for defining a fluid flow path from the metering station to the received fluid cartridge, with a one-way valve in said tubular member to prevent leakage of fluid from said tubular member when no fluid cartridge is present in said receiver;
      a biasing device interconnecting said interface device and the one portion for biasing the one portion away from said interface device to enlarge the size of the chamber of the metering station; and
      cartridge support structure for supporting the cartridge to be filled, said cartridge support structure establishing the final level the piston in the cartridge can attain upon the transfer of fluid into the cartridge to establish the maximum content of the fluid cartridge.

14. Apparatus according to claim 13 wherein the fluid cartridge orifice is covered with an openable flexible sheet, and has a wall defining an interior of the fluid cartridge, an opening at the end opposite the orifice and a movable piston disposed in the interior of the fluid cartridge and being movable away from the fluid cartridge orifice as the fluid cartridge is being filled, the final amount the piston can be moved away from the orifice determining the total amount of fluid admissible into the fluid cartridge, wherein said cartridge support structure comprises:
   a platform for supporting the fluid cartridge to be filled, said platform having a protrusion for extending into the end of a fluid cartridge opposite the orifice end of the fluid cartridge for establishing the maximum content of the fluid cartridge.

15. A system for filling fluid cartridges with fluid from a container, the cartridges having an orifice at one end and an opposing end, and a piston inside the cartridge for defining a fluid-containing portion between the piston and the orifice, the container having an interior and a fluid discharge outlet, the container discharging fluid through the discharge outlet in response to an air pressure differential across the fluid, said system comprising:

a holder for holding the container;

an air pressure differential apparatus for creating an air pressure differential across fluid in the container, said air pressure differential apparatus comprising:

walls defining a variable size chamber operatively connected to the container, said walls being movable to expand said chamber from a decreased size to create an air pressure differential across fluid in the container to draw fluid from the container, and said walls being movable to decrease the size of said chamber from an expanded size for forcing fluid withdrawn from the container into a cartridge and for equalizing the air pressure across fluid in the container.

16. A system according to claim 15 and further comprising:

a container holder wall structure connected to said holder and including chamber surfaces; and an interface device for receiving the fluid cartridge and for transferring fluid withdrawn from the container into the fluid cartridge;

wherein said walls defining a variable size chamber include said chamber surfaces of said container holder wall structure for defining one portion of said variable size chamber.

17. A system according to claim 16 wherein said interface device has interface surfaces for defining a second portion of said variable size chamber, said container holder wall structure and said interface device being movable in a first direction apart from each other to expand the size of said variable chamber to draw fluid into said chamber and admit air into the container to equalize the pressure across the fluid in the container, and being movable in a second direction towards each other to decrease the size of said variable chamber to force fluid from said chamber to said interface device and thereafter to the fluid cartridge.

18. A system according to claim 17 wherein said interface device comprises:

a receptacle for receiving a container said holder wall structure to define said variable size chamber; and a conduit for transferring fluid from said chamber to the fluid cartridge.

19. A system according to claim 18 wherein said holder and said container holder wall structure are movable in response to force applied to said holder, said receptacle receiving said container holder wall structure includes structure for receiving the fluid cartridge in position to receive fluid from said conduit.

20. A system according to claim 19 and further includes a biasing device for urging said container holder wall structure in the first direction to increase the size of said variable chamber.

21. A system according to claim 18 wherein said variable size chamber in the expanded size is able to hold at least enough fluid to fill the fluid cartridge, and said variable size chamber discharging sufficient fluid to fill the fluid cartridge received in said structure in response to the changing of said chamber from the expanded size to the decreased size.

22. A system according to claim 21 wherein said interface includes:

a wall structure receptacle for receiving said container holder wall structure;

a chamber body forming one of said walls defining part of said variable size chamber, said chamber body including a fluid conduit for transferring fluid from said variable size chamber to the fluid cartridge held in said fluid cartridge holding structure; and a spring structure in said wall structure receptacle for urging said container holder wall structure out of said receptacle to urge said variable size chamber to the expanded size;

said holder and said container holder wall structure moving into said wall structure receptacle and said wall structure with said chamber body decreasing the size of said variable size chamber in response to force being applied to move said holder towards said interface, to transfer fluid from said variable size chamber through said fluid conduit into the fluid cartridge.

23. A system according to claim 22 and further including:

a one-way valve in said fluid transfer channel for enabling the flow of fluid from the container and for preventing the flow of fluid back to the container from said variable size chamber through said fluid transfer channel.

24. A system according to claim 22 and further including:

a one-way valve in said fluid conduit for enabling the flow of fluid from said variable size chamber into the fluid cartridge and for preventing the flow of fluid through said fluid conduit from the fluid cartridge into said variable size chamber.

25. A system according to claim 16 wherein the collapsible container is a collapsible container containing fluid having a discharge opening for forcing the discharge of fluid from a discharge opening, wherein said interface has interface surfaces for defining a second portion of said variable size chamber, said container holder wall structure and said interface device being movable in a first direction to expand the size of said variable chamber to establish a suction at the discharge end of the collapsible container and pull fluid from the collapsible container into said chamber.

26. A system according to claim 25 wherein the collapsible container is a syringe having a movable piston for forcing the discharge of fluid from a discharge opening, wherein said interface device has interface surfaces for defining a second portion of said variable size chamber, said container holder wall structure and said interface device being movable in a first direction to expand the size of said variable chamber to establish a suction at the discharge end of the syringe and pull fluid from the syringe into said chamber, the piston following the movement of fluid from the syringe.

27. A system according to claim 25 wherein said interface device comprises:

a receptacle for receiving said holder wall structure to define said variable size chamber; and a conduit for transferring fluid from said chamber to the fluid cartridge.

28. A system according to claim 27 wherein said holder and said container holder wall structure are movable in response to force applied to said holder, said receptacle receiving said holder wall structure includes said interface device for receiving the fluid cartridge in position to receive fluid from said conduit.

29. A system according to claim 28 and further includes a biasing device for urging said container holder wall structure in the first direction to increase the size of said variable air chamber.

30. A system according to claim 28 wherein said fluid chamber is able to hold at least enough fluid to fill the fluid cartridge, and said fluid chamber discharging sufficient fluid to fill the fluid cartridge received in said interface device in response to the changing of said variable size air chamber from the expanded size to the decreased size.

31. A system according to claim 26 and further including:
a fluid transfer channel for receiving fluid from the syringe; and
a one-way valve in said fluid transfer channel for enabling the flow of fluid from the syringe and for preventing the flow of fluid from said fluid chamber through said fluid transfer channel.

32. A system according to claim 16 wherein the container is a syringe having a movable piston for forcing the discharge of fluid from a discharge end of the syringe, and wherein said variable size chamber is a variable size air chamber, wherein said system further includes a stationary device stationary with respect to said container holder wall structure and having said interface device, and wherein container holder wall structure further comprises:
first fluid chamber surfaces for defining one portion of a fluid chamber for receiving fluid from the syringe; and
a door structure for defining a second portion of said fluid chamber, said door structure having a closed condition for cooperating with first fluid chamber surfaces to form said fluid chamber, and an open condition for discharging fluid from said fluid chamber, said door structure assuming the open condition when a cartridge is received by said interface device;
said holder and said container holder wall structure being movable in response to force applied to said holder for forcing air from said variable size air chamber into the syringe held by said holder, and for discharging fluid from said fluid chamber into a fluid cartridge.

33. A system according to claim 15 wherein the container has a discharge orifice and a septum closing the orifice to hold fluid in the container, and said holder includes a piercing instrument for piercing the septum, and wherein said pressure differential apparatus comprises:
a fluid transfer channel for transferring fluid from the container to said variable size chamber; and
an air transfer channel for transferring air to the container as fluid is withdrawn from the container, in response to the piercing of the septum by said piercing instrument.

34. A system according to claim 33 wherein said instrument for piercing the septum is a spike, said fluid transfer channel extends through said spike interconnecting the containers and said chamber, and said air transfer channel extends through said spike interconnecting the container and the atmosphere.

35. A system according to claim 34 and further including a one-way valve for enabling air to enter the container and for preventing air and fluid from leaving the container.

36. A system according to claim 34 wherein said holder for holding the container receives the container in an inverted position with the septum facing downwardly towards the earth.

37. A system according to claim 15 wherein the fluid cartridges to be filled include an entrance having an inside surface and side walls and a bottom device, the bottom device having an inside surface and an exterior surface, the bottom device engaging the inside surface and being movable between an unfilled position near the entrance to the fluid cartridge and a bottom position, the bottom device assuming the bottommost position when the fluid cartridge is filled with fluid, and wherein said fluid cartridge holding structure includes a support for engaging the exterior surface of the bottom device of a fluid cartridge held by said fluid cartridge holding structure.

38. A system according to claim 16 wherein said variable size chamber is a variable size air chamber, wherein said system further includes a stationary device stationary with respect to said container holding wall structure and having air chamber surfaces for defining a second portion of said variable size air chamber, and wherein said container holder wall structure further comprises:
first fluid chamber surfaces for defining one portion of a fluid chamber for receiving fluid from the containers; and
a door structure for defining a second portion of said fluid chamber, said door structure having a closed condition for cooperating with said first fluid chamber surfaces to form said fluid chamber, and an open condition for discharging fluid from said fluid chamber, said door structure assuming the open condition when a fluid cartridge is received by said interface device;
said holder and said container holder wall structure being movable in response to force applied to said holder for forcing air from said variable size air chamber into the container held by said holder, and for forcing fluid from said fluid chamber.

39. A system according to claim 38 and further including:
biasing structure for biasing said holder and said container holder wall structure from a decreased condition wherein said variable size air chamber is in the decreased size to an expanded condition wherein said variable size air chamber is in the expanded condition.

40. A system according to claim 39 wherein said fluid chamber has a one-way valve for enabling fluid to enter said fluid chamber from the container and preventing fluid from flowing from said fluid chamber towards the container.

41. A system according to claim 40 wherein said fluid chamber holds a metered amount of fluid.

42. A system according to claim 38 wherein the container has a discharge orifice and a septum closing the orifice to hold fluid in the container, and said holder includes a piercing instrument for piercing the septum, and wherein said pressure differential apparatus comprises:
an air transfer channel for transferring pressurized air from said variable size air chamber into the container in response to said variable size air chamber assuming the decreased size; and
a fluid transfer channel for transferring fluid from the container to said fluid chamber in response to the transfer of pressurized air to the container.

43. A system according to claim 42 wherein said instrument for piercing the septum is a spike, said fluid transfer channel extends through said spike interconnecting the container and said fluid chamber, and said air transfer channel extends through said spike interconnecting the container and said variable size air chamber.

44. A system according to claim 43 wherein said fluid transfer channel has a one-way valve for enabling fluid to flow from a container into said fluid chamber and preventing the flow of fluid into the container, and said air transfer channel has a one-way valve for enabling air to be transferred into a container and for preventing air and fluid from leaving the container.

45. A system according to claim 15 and further including:
biasing structure for biasing said holder and said container holder wall structure from a decreased condition wherein said variable size air chamber is in the decreased size to an expanded condition wherein said variable size chamber is in the expanded size.

46. A system according to claim 45 wherein said chamber has a one-way valve for enabling fluid to enter said chamber for the container and preventing fluid from flowing from said fluid chamber towards the syringe.

47. A system according to claim 46 wherein said chamber holds a metered amount of fluid.

48. Apparatus for filling at least one fluid cartridge with a fluid, the at least one fluid cartridges having opposing ends, a fluid cartridge orifice in one of said ends, and a piston inside the fluid cartridge for defining a fluid container between the piston and the fluid cartridge orifice, the piston moving away from the orifice as fluid enters the container, said apparatus comprising:
 a housing for receiving a container holding the fluid, the container having a fluid discharge orifice covered by a septum;
 a septum opening device affixed to said housing and independent of the fluid cartridge(s) for severing the septum in response to the relative movement of the container with respect to said septum opening device; and
 cartridge support structure for supporting the cartridge to be filled, said cartridge support structure establishing the final level the piston in the cartridge can attain upon the transfer of fluid into the cartridge to establish the maximum content of the fluid cartridge.

* * * * *